United States Patent [19]

Schirmann et al.

[11] 3,943,132

[45] Mar. 9, 1976

[54] PROCESS FOR THE PREPARATION OF HYDRAZONES

[75] Inventors: Jean-Pierre Schirmann, Brignais; Henri Mathais, Ste. Foy-les-Lyon; Pierre Tellier, Oullins; Francis Weiss, Pierre-Benite, all of France

[73] Assignee: Produits Chimiques Ugine Kuhlmann, Paris, France

[22] Filed: Oct. 15, 1973

[21] Appl. No.: 406,467

[30] Foreign Application Priority Data
Oct. 16, 1972 France.............................. 72.36505

[52] U.S. Cl.. 260/247.5 R; 260/293.87; 260/296 R; 260/326.85; 260/345.1; 260/345.9; 260/465 E; 260/465.5 R; 260/516; 260/518 A; 260/558 H; 260/561 H; 260/566 B
[51] Int. Cl.².............. C07C 109/14; C07C 109/16; C07C 109/18
[58] Field of Search ................................ 260/566 B

[56] References Cited
UNITED STATES PATENTS
2,784,217    3/1957    Maute............................. 260/566 B

*Primary Examiner*—Gerald A. Schwartz
*Attorney, Agent, or Firm*—Pennie & Edmonds

[57] ABSTRACT

This invention relates to a method of preparing hydrazones of the formula

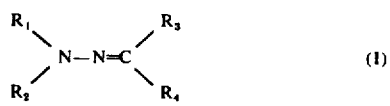

(I)

in which $R_1$ and $R_2$, which may be identical or different, represent a linear alkyl radical of from 1 to 12 carbon atoms, a branched alkyl or cycloalkyl radical of from 3 to 12 carbon atoms, an aromatic radical of from 6 to 12 carbon atoms having a benzene or naphthalene nucleus, or a radical of from 5 to 12 carbon atoms having a pyridine nucleus, or $R_1$ and $R_2$ together form a linear or branched alkylene radical of from 3 to 12 carbon atoms in which one of the carbon atoms of the chain may be replaced by an oxygen atom, all of the above radicals being unsubstituted or substituted by one or more atoms or groups such as chlorine, bromine, fluorine, or iodine atoms or hydroxy, ether, carboxylic acid, carboxylic amide or ester, nitrile, nitro, or sulphonic acid or amide groups, or one of the two radicals $R_1$ and $R_2$ may be a hydrogen atom, and in which $R_3$ and $R_4$, which may be identical or different, represent a hydrogen atom, a linear alkyl or cycloalkyl radical of from 3 to 12 carbon atoms, in which one of the carbon atoms of the cycloalkyl radical may be replaced by an oxygen atom, or an aromatic hydrocarbon radical of from 6 to 12 carbon atoms or $R_3$ and $R_4$ together represent a linear or branched alkylene radical of from 3 to 11 carbon atoms, the above radicals being unsubstituted or substituted by atoms or groups such as chlorine, bromine, fluorine, ethylenic groups, nitro, hydroxy, alkoxy, or carboxylic acid or ester radicals, which comprises reacting a primary or secondary amine of the formula

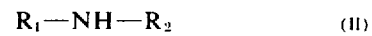

wherein $R_1$ and $R_2$ are as defined above, ammonia, and a carbonyl compound of the formula

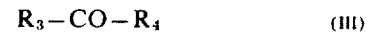

wherein $R_3$ and $R_4$ are as defined above, with a peroxide compound.

2 Claims, No Drawings

PROCESS FOR THE PREPARATION OF HYDRAZONES

BACKGROUND OF THE INVENTION

I. Field of the Invention

This invention relates to the preparation of hydrazones and specifically to the preparation of hydrazones by the method of reacting a primary or secondary amine, ammonia, and a carbonyl compound with a peroxide compound.

II. Description of the Prior Art

From numerous publications it is known that the primary or secondary amines are easily oxidized by peroxide compounds into very diverse oxygenated products, such as hydroxyl amines, nitroso or nitrated derivatives, oximes, compounds having an azoxy function, amides, etc., depending on the particular structure of the reactants or the reaction conditions. Thus, a description has been given of the oxidation of primary aliphatic amines to nitroalkanes by peracetic acid (W. D. Emmons, J. Am. Chem. Soc., 79, 5528, 1957) or other percarboxylic acids (see for example the paper by H. O. Larson in "The Chemistry of the Nitro and Nitroso Groups", part I, p. 309, published by H. Feuer, Interscience, New York, 1969).

The primary aromatic amines have been oxidized into the corresponding nitroso, nitro, or azoxy derivatives by the pure percarboxylic acids or by a mixture of acetic acid and a 30% aqueous solution of hydrogen peroxide (R. R. Holmes and R. P. Bayer, J. Am. Chem. Soc., 82, 3454, 1960; see also the paper by W. M. Weaver in "The Chemistry of the Nitro and Nitroso Groups." part 2, p. 29, published by H. Feuer, Interscience, New York, 1970). Aniline has also been oxidized into azoxybenzene by hydrogen peroxide in the presence of acetonitrile (G. B. Payne, P. H. Deming and P. H. Williams, J. Org. Chem., 26, 659, 1961). The oxidation of secondary amines into the corresponding hydroxyl amines has, for example, been effected by means of diacyl peroxides (French Pat. No. 1,360,030), of hydrogen peroxide in the presence of formic acid esters (German Pat. No. 1,004,191), or of hydrogen peroxide in the presence of nitriles (F. C. Schaefer and W. D. Zimmermann, J. Org. Chem., 35, 2165, 1970).

In previous patents and applications for patents the applicants have moreover described new processes for the synthesis of azines by oxidation of ammonia in the presence of a carbonyl compound (III) with one of the peroxide compounds mentioned above, in accordance with the general reaction

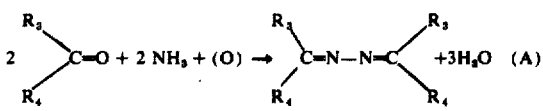 (A)

The oxidizing agent can be a percarboxylic acid (IV) (pending U.S. application Ser. No. 290,507, filed Sept. 20, 1972), a diacyl peroxide (V) (pending U.S. application Ser. No. 308,836, filed Nov. 22, 1972), hydrogen peroxide in the presence of salts (VI) as catalysts (pending U.S. application Ser. No. 267,921, filed June 30, 1972), hydrogen peroxide in the presence of nitriles (VII) as co-reactants (French Pat. 2,092,734, applied for June 12, 1970, and pending U.S. application Ser. No. 152,413, filed June 11, 1971), hydrogen peroxide in the presence of esters (VII) as co-reactants (pending U.S. application Ser. No. 340,762, filed Mar. 13, 1972), a hydrogen peroxide in the presence of amides or imides (IX) as co-reactants (pending U.S. application Ser. No. 341,057, filed Mar. 14, 1972), and hydrogen peroxide in the presence of cyanogen compounds (X) as co-reactants (pending U.S. application Ser. No. 340,762, filed Mar. 13, 1972).

SUMMARY OF THE INVENTION

It has been surprisingly discovered that the hydrazones of this invention can be prepared by reacting a peroxide compound, a primary or secondary amine, and ammonia with a carbonyl compound.

Broadly, the method of this invention is one of preparing hydrazones of the formula

 (I)

in which $R_1$ and $R_2$, which may be identical or different, represent a linear alkyl radical of from 1 to 12 carbon atoms, a branched alkyl or cycloalkyl radical of from 3 to 12 carbon atoms, an aromatic radical of from 6 to 12 carbon atoms having a benzene or naphthalene nucleus, or a radical of from 5 to 12 carbon atoms having a pyridine nucleus, or $R_1$ and $R_2$ together form a linear or branched alkylene radical of from 3 to 12 carbon atoms in which one of the carbon atoms of the chain may be replaced by an oxygen atom, all of the above radicals being unsubstituted or substituted by one or more atoms or groups such as chlorine, bromine, fluorine, or iodine atoms or hydroxy, ether, carboxylic acid, carboxylic amide or ester, nitrile, nitro, or sulfonic acid or amide groups, or one of the two radicals $R_1$ and $R_2$ may be a hydrogen atom, and in which $R_3$ and $R_4$, which may be identical or different, represent a hydrogen atom, a linear alkyl radical of from 1 to 12 carbon atoms, a branched alkyl or cycloalkyl radical of from 3 to 12 carbon atoms, in which one of the carbon atoms of the cycloalkyl radical may be replaced by an oxygen atom, or an aromatic hydrocarbon radical of from 6 to 12 carbon atoms or $R_3$ and $R_4$ together represent a linear or branched alkylene radical of from 3 to 11 carbon atoms, the above radicals being unsubstituted or substituted by atoms or groups such as chlorine, bromine, fluorine, ethylenic groups, nitro, hydroxy, alkoxy, or carboxylic acid or ester radicals, which comprises reacting a primary or secondary amine of the formula

 (II)

wherein $R_1$ and $R_2$ are as defined above, ammonia, and a carbonyl compound of the formula

 (III)

wherein $R_3$ and $R_4$ are as defined above, with a peroxide compound.

DESCRIPTION OF THE PREFERRED EMBODIMENTS

This invention relates to a method of preparing hydrazones of the formula

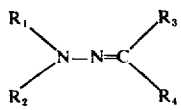 (I)

in which $R_1$ and $R_2$, which may be identical or different, represent a linear alkyl radical of from 1 to 12 carbon atoms, a branched alkyl or cycloalkyl radical of from 3 to 12 carbon atoms, an aromatic radical of from 6 to 12 carbon atoms having a benzene or naphthalene nucleus, or a radical of from 5 to 12 carbon atoms having a pyridine nucleus, or $R_1$ and $R_2$ together form a linear or branched alkylene radical of from 3 to 12 carbon atoms in which one of the carbon atoms of the chain may be replaced by an oxygen atom, all of the above radicals being unsubstituted by one or more atoms or groups such as chlorine, bromine, fluorine, or iodine atoms or hydroxy, ether, carboxylic acid, carboxylic amide or ester, nitrile, nitro, or sulphonic acid, or amide groups, or one of the two radicals $R_1$ or $R_2$ may be a hydrogen atom, and in which $R_3$ and $R_4$, which may be identical or different, represent a hydrogen atom, a linear alkyl radical of from 1 to 12 carbon atoms, a branched alkyl or cycloalkyl radical of from 3 to 12 carbon atoms, in which one of the carbon atoms of the cycloalkyl radical may be replaced by an oxygen atom, or an aromatic hydrocarbon radical of from 6 to 12 carbon atoms or $R_3$ and $R_4$ together represent a linear or branched alkylene radical of from 3 to 11 carbon atoms, the above radicals being unsubstituted or substituted by atoms or groups such as chlorine, bromine, fluorine, ethylenic groups, nitro, hydroxy, alkoxy, or carboxylic acid or ester radicals, which comprises reacting a primary or secondary amine of the formula

 (II)

wherein $R_1$ and $R_2$ are as defined above, ammonia, and a carbonyl compound of the formula

 (III)

wherein $R_3$ and $R_4$ are as defined above, with a peroxide compound selected from the percarboxylic acids

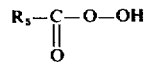 (IV)

where $R_5$ may represent a hydrogen atom, a linear alkyl radical of from 1 to 18 carbon atoms, a branched alkyl or cycloalkyl radical of from 3 to 12 carbon atoms, the above radicals being unsubstituted or substituted by groups such as the ethylenic groups, chloro, bromo, fluoro, nitro, hydroxy, alkoxy, carboxylic acid, amide, nitrile, or carboxylic ester groups; a diacyl peroxides (also known as the acyl peroxides), which have one or more of the functional groups

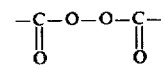 (V)

such as in

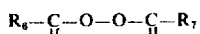 (Va)

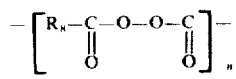 (Vb)

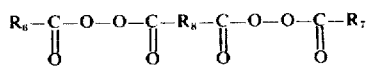 (Vc)

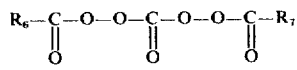 (Vd)

in which $R_6$ and $R_7$ each preferably represents a linear alkyl radical of from 1 to 18 carbon atoms, a branched alkyl or cycloalkyl radical of from 3 to 18 carbon atoms, an aromatic hydrocarbon radical of from 6 to 18 carbon atoms, a radical having a 5-6 membered oxygen or nitrogen heterocyclic ring and having 4 to 18 carbon atoms, or an alkoxy radical of from 1 to 18 carbon atoms, in which $R_6$ and $R_7$ may also be combined to represent together an 1,2-alkylene radical of from 2 to 18 carbon atoms or an 1,2-alkylene radical of from 6 to 18 carbon atoms, and in which $R_8$ may either not exist or may represent a linear alkylene radical of from 2 to 10 carbon atoms, a branched or cyclic alkylene radical of from 6 to 12 carbon atoms, all of the above radicals being unsubstituted or substituted by ethylenic theylenic groups, chloro, bromo, fluoro, nitro, hydroxy, alkoxy, carboxylic or percarboxylic acid, amide, nitrile, or carboxylic ester groups, etc., and the value of n in the polymer peroxides of formula (Vb) may range from 2 to approximately 30; and hydrogen peroxide, which is used in the presence of a certain salt (VI) acting as a catalyst or of a co-reactant selected from the nitriles (VII), esters (VIII), amides or imides (IX) of carboxylic acids, or cyanogen compounds (X) defined below, or of both a salt and a co-reactant.

The salts (VI) which can be used as catalysts for the reaction with hydrogen peroxide are preferably selected from the soluble salts or hydroxides of ammonium or of metals of Groups Ia and IIa of the Periodic Table.

The nitriles (VII) which can be used as co-reactants of hydrogen peroxide may be represented by the general formula

 (VII)

and comprise mono and polynitriles, in which p has a value of from 1 to 6 and in which $R_9$ is a hydrocarbon radical of valence p which has up to 12 carbon atoms and which may be aliphatic or alicyclic or which may have a benzene or pyridine ring, being unsubstituted or substituted by from 1 to 6 identical or different groups, such as the ethylenic groups, amide, carboxylic acid or ester, nitro, primary amine, secondary amine, tertiary amine, nitroso, fluoro, chloro, bromo, iodo, hydroxy, ether, acetal, epoxy sulphoxide, sulphone, or sulphonic acid groups.

The esters (VIII) which can be used as co-reactants of hydrogen peroxide may be represented by the general formula

 (VIII)

and can be selected from the monofunctional esters of monoalcohols $R_{11}$ - OH, in which $R_{11}$ represents a linear, branched, or cyclic hydrocarbon radical of up to about 12 carbon atoms, or of phenols $R_{11}$ - OH, in which $R_{11}$ represents a phenyl group, and of carboxylic monoacids $R_{10}$-COOH, in which $R_{10}$ represents either a hydrogen atom or a linear or branched alkyl, cycloalkyl, aryl-alkyl, or aromatic group of up to about 12 carbon atoms, or the polyfunctional esters of monoalcohols or of phenols $R_{11}$ - OH and of carboxylic polyacids $R'_{10}$ (-COOH)$_q$, in which $q$ is an integer of from 2 to 6 and $R'_{10}$ is either a simple bond ($q$ being in this case equal to 2 exclusively) or a linear, branched, or cyclical alkyl radical or aromatic radical of valence $q$ and having up to about 12 carbon or the polyfunctional esters of carboxylic monoacids $R_{10}$COOH and of polyols or of polyphenols $R'_{11}$(OH)$_r$, in which r is an integer of from 2 to 6 and $R'_{11}$ is an aliphatic or aromatic hydrocarbon radical of valence r and having up to about 12 carbon atoms, or the cyclic esters of carboxylic hydroxy acids, such as the lactones, in which the radicals $R_{10}$ and $R_{11}$ together represent a linear or branched alkylene radical of from 2 to 11 carbon atoms and, together with the carboxylic group, form lactonic cycles of from 4 to 12 links, or the cyclic or acyclic oligomers of these lactones. The radicals $R_{10}$, $R_{11}$, $R'_{10}$, and $R'_{11}$ may optionally have substituents, such as the ethylenic groups, chloro, bromo, fluoro, nitro, alkoxy, hydroxy, or carboxylic acid or amide groups, the number of which does not exceed 6.

The amides and imides (IX) which can be used as coreactants of hydrogen peroxide are selected among the amides and imides of the carboxylic monoacids or polyacids having an ionization constant lower than about $5 \times 10^{-5}$.

The cyanogen compounds (X) which can be used as coreactants of hydrogen peroxide are selected from a group composed of the single or complex salts of hydrocyanic, cyanic, and thiocyanic acids, the halides, the amides and esters of cyanic acid, and the oligomers of the derivatives of cyanic acid mentioned above.

The invention generally proceeds according to the reaction

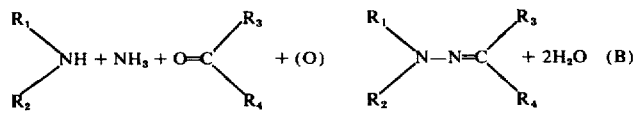

and the origin of the active oxygen (O) can be explained by a partial equation dependent on the peroxide system or compound used, such as

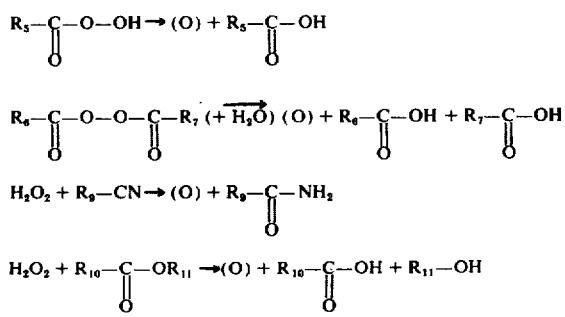

Thus, the percarboxylic acids and acyl peroxides are converted during the reaction into the corresponding carboxylic acids, forming ammonium salts in the reaction medium.

When hydrogen peroxide is used with the co-reactants mentioned, they form an intermediate active oxidizing species, the nature of which has not been explained and the conversion of which leads finally to the hydration or hydrolysis products of the co-reactant, such as, for example, an amide when the starting material is a nitrile, and carboxylic acid in the form of the ammonium salt when the starting material is an ester or an amide.

The hydrazones thus obtained are useful synthesis agents which can be used instead of the corresponding substituted hydrazines, or which can be hydrolyzed in known manner to obtain the dissymmetrical substituted hydrazines or their salts according to

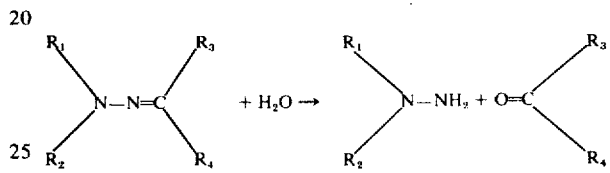

The reaction of formation of hydrazones (B) may be accompanied, in variable proportions, by the formation of azines according to the general reaction (A). Since these azines are valuable products which can be hydrolyzed to obtain the nonsubstituted hydrazine, the joint production of hydrazones and azines may be advantageous and constitute and additional aim of the present invention.

The following are examples of reactants or catalysts which can be used within the scope of the present invention:

amines (II):
methylamine, dimethylamine, ethylamine, diethylamine, n-propyl amine, isopropylamine, n-butylamine, di-n-butylamine, t-butylamine, the amylamines, cyclohexylamine, dicyclohexylamine, n-dodecylamine, mono- and diethanolamines, methoxy-2-ethylamine, morpholine, pyrrolidine, piperidine, β-aminopropionitrile, β-aminopropionamide, aniline, the toluidines, the mono- and dichloro-anilines or -toluidines, the bromoanilines, the fluoro-anilines, the nitro- and dinitro-anilines and -toluidines, the o- m- and p-anisidines, the trifluoromethylanilines, anthranilic acid, sulphanilic acid, diphenylamine, α-naphthylamine, β-naphthylamine, the aminopyridines;

carbonyl compounds (III):
aldehydes: formaldehyde, acetaldehyde, propionaldehyde, butyraldehyde, isobutyraldehyde, n-pentanal, pivalaldehyde, oenanthal, ethyl-2hexanal, Δ -3-tetrahydrobenzaldehyde, hexahydrobenzaldehyde, 5-norbornene 2-carboxaldehyde, tetrahydropyrane-2-carboxaldehyde, benzaldehyde, the monochlorobenzaldehydes, p-nitrobenzaldehyde, β-chloropropionaldehyde, β-methoxypropionaldehyde, 4-cyano-2,2-dimethylbutyraldehyde. ketones: acetone, 2-butanone, 2-pentanone, 3-pentanone, methylisopropylketone, methylisobutylketone, ethylamylketone, methylcyclohexylketone, acetophenone, benzophenone, cyclobutanone, cyclopentanone, cyclohexanone, 2-methyl, cyclohexanone, 3-methyl, cyclohexanone, 4-methyl cyclohexanone, 2,4-dimethyl cyclohexanone, 3,3,5-trimethyl, cyclohexanone, isophorone, cycloheptanone, cyclooctanone, cyclodecanone, cyclododecanone;

percarboxylic acids (IV) derived from carboxylic acids: formic, acetic, propionic, butyric, isobutyric, valeric, isovaleric, pivalic, hexanoic, heptanoic, octanoic, αα′-dimethyloctanoic, lauric, palmetic, stearic, hexahydrobenzoic, trifluoroacetic, β-chloropropionic, β-methoxypropionic, ε-hydroxycaproic acids, benzoic acid and its ortho-, meta-, or para- chlorine, bromine, fluorine, methoxyl, nitro, or trifluoro-methyl derivatives, o-, m-, and p-toluic, succinic, glutaric, adipic, crotonic, maleic, fumaric, phthalic acids;

diacyl peroxides (V):

among the peroxides of formula (Va); acetyl, monochloroacetyl, trifluoroacetyl, propionyl, β-chloropropionyl, β-methoxypropionyl, β-carboxypropionyl, n-butyryl, perfluoro-n-butyryl, isobutyryl, perfluoroisobutyryl, crotonyl, valeryl, isovaleryl, pivaloyl, hexanoyl, heptanoyl, octanoyl, ethyl-2 hexanoyl, nonanoyl, decanoyl, lauroyl, myristoyl, palmitoyl, stearyl, cyclohexanecarbonyl, norbornane-2 carbonyl, benzoyl, o-toluyl, m-chlorobenzoyl, p-chlorobenzoyl, p-methoxybenzoyl, p-nitro-benzoyl, m-trifluoromethyl benzoyl, p-phenylbenzoyl, o-carboxyl-benzoyl, α-naphthoyl, β-naphthoyl, 2-furoyl, and nicotinoyl peroxides or mixed peroxides such as acetyl and benzoyl peroxides, acetyl and butyryl peroxides, isobutyryl and benzoyl peroxides, acetyl and lauroyl peroxides, or stearyl and benzoyl peroxides; polymeric peroxides (Vb) and mixed peroxides of mono- and diacids (Vc) derived from HOOC - R8 -COOH diacid, oxalic (in which $R_8$ does not exist), succinic, glutaric, adipic, pimelic, dodecanedioic, 1,2 or 1,4-cyclohexane dicarboxylic, o-phthalic, isophthalic, terephthalic; peroxides (Va) derived from carbonic acid, in which at least one of the radicals $R_6$ and $R_7$ is an alkoxy group, such as isopropoxycarbonyl and benzoyl peroxide, methoxycarbonyl and lauroyl peroxide, 3,3,5-trimethyl, cyclohexyloxycarbonyl and lauroyl peroxide, isopropyl peroxydicarbonate. mixed peroxides (Va) such as the mixed dianhydrides of diperoxycarbonic and benzoyl, caproyl, lauroyl, or 2-ethyl hexanoyl;

salts (VI) where these are soluble:

chlorides, bromides, fluorides, nitrates, sulphates, phosphates, chlorates, perchlorates, borates, carbonates, formiates, acetates, propionates, butyrates, isobutyrates, octanoates, benzoates, methanesulphonates, benzenesulphonates, p-toluenesulphonates of lithium, sodium, potassium, magnesium, calcium, strontium, barium, and ammonium, which latter may be derived from ammonia or from a mono-, di-, or trialkylated amine, in which the alkyl radicals contain from 1 to 12 carbon atoms, or from a cyclic secondary amine, such as piperidine, morpholine, or pyrrolidine.

nitriles (VII):

acetonitrile, propionitrile, butyronitrile, isobutyronitrile, cyclohexylcarboxylic nitrile, benzonitrile, o-, m-, or p- tolunitrile, p-methoxybenzonitrile, chlorobenzonitrile, p-nitrobenzonitrile, mono-, di-, and trichloroacetonitrile, glycolonitrile, ε-hydroxycapronitrile, cyanacetic acid and its alkyl esters, β-cyanopropionic acid and its alkyl esters, β-cyanopyridine, nicotinic nitrile, isonicotinic nitrile, acrylonitrile, methacrylonitrile, crotononitrile, Δ-3-tetrahydrobenzonitrile, 3,4-epoxy hexahydrobenzonitrile, ββ′-dicyanoethylether, ββ′-dicyanoethyl sulphide, sulphoxide, or sulphone, cyanogen, malononitrile, succinonitrile, glutaronitrile, adiponitrile, pimelonitrile, suberonitrile, phthalodinitriles, iminodiacetonitrile, nitrolotriacetonitrile, ethylenediaminetetracetic acid nitrile, βhydroxypropionitrile, β-methoxypropionitrile, and the cyanoethyl derivatives of ethyleneglycol, glycerol, and sorbitol.

carboxylic esters (VIII):

formiates, acetates, monochloracetates, trichloracetates, trifluoroacetates, propionates, butyrates, isobutyrates, valerates, hexanoates, octanoates, nonanoates, dodecanoates, benzoates, o-, m-, or p-chlorobenzoates, p-methoxybenzoates, nitrobenzoates, oxalates, malonates, succinates, glutarates, adipates, pimelates, butane-1,2,4-tricarboxylates, o-phthalates, isophthalates, terephthalates, trimellitates, pyromellitates, β-hydroxypropionates, tartrates or citrates of methanol, ethanol, n-propanol, isopropanol, n-butanol, isobutanol, 2-butanol, tertiary butanol, amyl alcohols, n-hexanol, n-heptanol, n-octanol, 2-ethyl hexanol, n-dodecanol, cyclohexanol, methylcyclohexanol, allyl alcohol, crotyl alcohol, Δ-3-tetrahydrobenzyl alcohol, benzyl alcohol, 2-methoxy ethanol, 3-methoxy propanol, 2-ethoxy ethanol, ethyleneglycol, propyleneglycol, glycerol, 1,1,1-trimethylol ethane, pentaerythritol, sorbitol, phenol and its chlorine, bromine, nitro, and methoxyl derivatives, cresols, pyrocatechol, resorcinol, and hydroquinone, and the lactones β-propiolactone, γ-butyrolactone, δ-valerolactone, ε-caprolactone, and their alkyl homologues;

amides or imides (IX):

formamides, monochloroacetamide, monobromoacetamide, dichloroacetamide, trichloroacetamide, trifluoroacetamide, β-chloropropionamide, αα-dichloropropionamide, α-bromopropionamide, perfluorobutyramide, gylcolamide, lactamide, phenylacetamide and its derivatives halogenated in the core, diphenylacetamide, benzamide, o-toluamide, m-toluamide, o-, m-, or p-chlorobenzamide, o-, m-, or p-bromobenzamide, o-, m-, or p-flurobenzamide, perfluorobenzamide, o-, m-, or p-nitrobenzamide, salicylamide, p-hydroxybenzamide, the monoamides, diamides, or the cyclic imides of the following di-,tri-, or tetracids: oxalic malonic succinic, αα-dichlorosuccinic, malic, tartric, maleic, citric, itaconic, citraconic, o-phthalic, isophthalic, terephthalic, trimellitic, pyromellitic, tetrachloro-o-phthalic;

cyanogen compounds and their derivatives (X):

the cyanides, cyanates, or thiocyanates of ammonium, alkali metals, or alkaline earth metals, magnesium, or zinc, the complex cyanides such as potassium ferrocyanide, cyanogen chloride and bromide, cyanamide and its alkali metal or alkaline earth metal salts, the lower alkyl cyanates in which the alkyl group contains from 1 to 6 carbon atoms approximately, the phenyl cyanates, dicyandiamide, the salts and esters of cyanuric and isocyanuric acids, cyanuric halides, and melamine.

For the purpose of carrying out the process according to the invention the reactants are brought into contact in a liquid medium by mixing them in any order or in any combination. The use of a solvent is generally advantageous or necessary in order to homogenize the reaction medium at least partially. The preferred solvents are water, or saturated alcohols of from 1 to 6 carbon atoms, particularly when the peroxide compound used is hydrogen peroxide, percarboxylic acid, or a lower acyl peroxide, but is may also be necessary to use non-polar solvents in order to solubilize certain percarboxylic acids or acyl peroxides, and in that case these solvents can then be selected from the aliphatic, cycloaliphatic, or aromatic hydrocarbons of from 5 to 12 carbon atoms, halogenated solvents such as methylene chloride, chloroform, carbon tetrachloride, dichlorethane, chlorobenzene, the ethers such as diethylether, dioxan, tetrahydrofuran, and nitro solvents such as nitromethane and nitrobenzene.

The preferred reaction temperature is approximately between −20° and 100° C, while the optimal value may vary according to the particular reactivity of the reactants used. It is possible to operate at atmospheric pressure or else at a pressure ranging up to 10 atmospheres, if that is necessary to keep the reactants in solution, particularly in the case of ammonia.

The reactants are advantageously used in stoichiometrical proportions, but there may be a deficiency or an excess of one or the other of them in relation to these proportions. The ammonia and the amine amy be used in a molar ratio between about 1:10 and 10:1, and the total of these two reactants is preferably in excess in relation to the peroxide compound; the molar ratio (ammonia + amine) / (oxide compound) may thus be between about 10:1 and 1:1. It may be necessary to add to these proportions the amount of ammonia or amine required to neutralize the acidity produced by the reaction with certain peroxide compounds, as indicated in the formula above. The carbonyl compound is used at the rate of from 0.1 to 10 moles per mole of (ammonia + amine).

When the peroxide compound used is hydrogen peroxide the operation is carried out as described in the presence of a salt as a catalyst, the latter being added at the rate of from 0.01 to 10% by weight of the total mixture of the reaction, and/or in the presence of a co-reactant, such as a nitrile, an ester, a carboxylic acid amide or imide, or a cyanogen compound, which is used at the rate of from 1 to 10 moles per mole of $H_2O_2$.

The reactants may be used in their usual commercial form, in the pure state, or dissolved in water or in a solvent; for example, ammonia, the lower aliphatic amines, and hydrogen peroxide may be used in the form of commercially available aqueous solutions. They may also be prepared by known methods, the diacyl peroxides or peracids being, for example, prepared by reacting an acyl halide or an acid anhydride with hydrogen peroxide or sodium peroxide, or the lower percarboxylic acids may be prepared by reacting hydrogen peroxide with the corresponding carboxylic acid, possibly in the presence of a small catalytic amount of sulphuric acid. Since this reaction is in equilibrium, it is also possible to use the crude mixture of the equilibrium reaction, particularly crude mixtures containing performic acid or peracetic acid which are obtained by reacting hydrogen peroxide with formic or acetic acid.

The following examples illustrate the present invention, but do not restrict it.

EXAMPLE 1

A solution was prepared which comprised 149 g aniline (1.6 mole), 36 g of an ammonia solution having 22% by weight $NH_3$ (0.46 mole), 23.2 g acetone (0.4 mole), 41 g acetonitrile (1 mole) in 64 g methanol, 0.4 g ammonium acetate, and 2 g of the disodium salt of ethylenediaminetetracetic acid. The solution was heated to 50° C., and 41 g of a 70% by weight aqueous solution of hydrogen peroxide (0.8 mole) and 92.8 g acetone (1.6 mole) were added, dropwise and simultaneously. The solution was than kept at 50° C for 5 hours while a light current of gaseous ammonia was bubbled through it. The unreacted methanol, ammonia, acetone, and acetonitrile were eliminated by distillation in vacuo, and the remaining solution was washed three times with an equal volume of water. The organic layer was decanted and distilled. After eliminating the excess aniline, 48 g of acetone phenylhydrazone (0.32 mole, which was 40% of the theoretical yield, compared to the hydrogen peroxide used), which was identified by comparison of its infrared spectrum with that of the compound obtained by the action of phenylhydrazine on acetone, were collected at 163–165° C and 50 mm Hg.

EXAMPLE 2

A crude peracetic acid solution was prepared by mixing 17.3 g glacial acetic acid (0.29 mole), 7.2 g of a hydrogen peroxide solution having 68% by weight of $H_2O_2$ (0.145 mole of $H_2O_2$), and 0.7 g concentrated sulphuric acid, and reacting the mixture for several hours at ambient temperature. A solution was obtained which contained 0.10 mole peracetic acid and 0.033 mole uncoverted hydrogen peroxide, and which was introduced into 200 ml of methanol at 0° C. Within the space of half an hour 34.8 g acetone (0.6 mole), 12.2 g of an ammonia solution having 28% by weight $NH_3$ (0.2 mole), and 18.6 g aniline (0.2 mole) were added, after which the mixture was determined by gas phase chromatography to contain 4.6 g of acetone phenylhydrazone (0.031 mole, which was 31% of the theoretical yield compared to the peracid), 1 g of acetone azine (0.009 mole, which was 9% of the theoretical yield), and 0.025 mole of azobenzene.

EXAMPLE 3

Potassium monopermaleate was prepared by introducing at 20° C 18.4 g of a 65% by weight aqueous solution of caustic potash (0.22 mole) in a solution of 21.5 g maleic anhydride (0.22 mole) and 11.7 g aqueous hydrogen peroxide containing 70% by weight $H_2O_2$ (0.24 mole) in 120 cc ethyl acetate. The mixture was kept at 20° C for 1 hour, whereupon the per-salt was filtered and dried at atmospheric temperature.

20 g of this crude product, which has 0.10 mole potassium monopermaleat and 0.02 mole hydrogen peroxide, were suspended in 200 ml methanol at 0° C. Within the space of half an hour 34.8 g acetone (0.6 mole), 12.2 g of an ammonia solution having 28% $NH_3$ (0.2 mole), and 18.6 g aniline (0.2 mole) were added, whereupon the mixture was allowed to return to ambient temperature.

One hour after the start of the addition, the reaction mixture was determined by gas phase chromatography to contain 6.4 g actone phenylhydrazone (0.043 mole, which was 43% of the theoretical yield compared to the peracid), 1.25 g acetoneazine (0.011 mole, which was an 11% yield), and 0.003 mole azobenzene.

EXAMPLE 4

18.3 g p-nitroperbenzoic acid (0.10 mole) were dissolved in 200 ml methanol. Within the space of half an hour 34.8 g acetone (0.6 mole), 12.2. g of an ammonia solution having 28% by weight $NH_3$ (0.2 mole), and 18.6 g aniline (0.2 mole) were added at 0° C, whereupon the mixture was allowed to return to ambient temperature. One hour after the start of the addition, the mixture was determined by gas phase chromatography to contain 2.92 g actone phenylhydrazone (0.197 mole, which was 19.7% of the theoretical yield compared to the peracid) and 0.45 g acetoneazine (0.004 mole, which was a 4% yield).

EXAMPLE 5

A solution was prepared which comprised 56 g aniline (0.60 mole), 20 g ammonia (1.8 mole), 35 g acetone (0.60 mole), and 0.75 g of the disodium salt of ethylenediamine tetracetic acid in 120 g methanol and 15 g water. Within 25 minutes, 86 g of 84.2% benzoyl peroxide (0.30 mole) were introduced at 20° C, and the mixture was then kept for 30 minutes at the same temperature. The salts which precipitated were filtered and the solution was determined by gas chromatography to contain 13.3 g acetone phenylhydrazone (0.09 mole, which was 30% of the theoretical yield compared to the benzoyl peroxide), 5.4 g acetoneazine (0.048 mole, which was a yield of 16%), and 0.006 mole azobenzene.

EXAMPLE 6

The operation was carried out as in Example 5, but 162 g of 58% nonanoyl peroxide (0.3 mole; commercial product of Societe Chalonnaise de Peroxydes Organiques) were used instead of benzoyl peroxide. The final solution was determined by gas phase chromatorgraphy to comprise 14.3 g acetone phenylhydrazone (0.097 mole, which was 32.3% of the theoretical yield), 5.85 g acetoneazine (0.052 mole, which was a 17.4% yield), and traces of azobenzene.

EXAMPLE 7

The procedure was the same as in Example 5, but 286 g of a 22% solution of isopropyl peroxydicarbonate in dibutylphtalate (0.30 mole) were used instead of benzoyl peroxide. A gas phase chromatography determination of the final solution showed that 12.6 g acetone phenylhydrazone (0.085 mole, which was 28.4% of the theoretical yield), 1.12 g acetoneazine (0.01 mole, which was a yield of 3.3%), and 0.022 mole azobenzene were formed.

EXAMPLE 8

The procedure was the same as in Example 5, but 97.5 g of 88% cyclohexyl peroxydicarbonate (0.30 mole; commercial product of Société Châlonnaise de Peroxydes Organiques) were used instead of benzoyl peroxide. Determination by gas phase chromatography of the final solution showed that 21.3 g acetone phenylhydrazone (0.144 mole, which was 48% of the theoretical yield), 6.2 g acetoneazine (0.055 mole, which was a yield of 18.3%), and 0.12 mole azobenzene were formed.

EXAMPLE 9

A solution was prepared which comprised 93 g aniline (1 mole), 4.25 g ammonia (0.25 mole), 14.5 g acetone (0.25 mole), 6.15 g aqueous hydrogen peroxide containing 69% by weight $H_2O_2$ (0.125 mole), and 1.25 g of the disodium salt of ethylnediaminetetracetic acid in 22.5 g water and 40 g methanol. This solution was brought to 50° C, whereupon during 1 hour, 15.3 g gaseouos ammonia (0.9 mole), 18.45 g aqueous hydrogen peroxide containing 68% by weight $H_2O_2$ (0.375 mole), 43.5 g acetone (0.75 mole), and 28.1 g formamide (0.625 mole) were introduced simultaneously. After reacting the mixture for another hour at the same temperature, analysis of the mixture by gas phase chromatography showed that 33.0 g acetone phenylhdrazone (0.223 mole, which was 44.6% of the theoretical yield) were formed. The mixture was allowed to cool to ambient temperature, and the two liquid phases which formed were separated by decantation. The light organic phase weighing 165 g was separated by fractional distillation at 130°–140° C and 10 mm Hg, and 30 g acetone phenylhydrazone were collected.

EXAMPLE 10

A solution was prepared which comprised 24.8 g monomethylamine (0.80 mole), 13.6 g ammonia (0.80 mole), 46.4 g acetone (0.80 mole), 16.4 g acetonitrile (0.40 mole), and 0.4 g of the disodium salt of ethylenediaminetetracetic acid in 128 g methanol and 60 g water. The solution was brought to 30°C, whereupon within one hour 19.6 g oxygenated water containing 69.3% by weight $H_2O_2$ (0.40 mole) were introduced. The reaction was then allowed to continue for 3 hours at the same temperature, and the mixture was determined by gas phase chromatography to contain 4.15 g acetone methylhydrazone (0.048 mole, which was 12% of the theoretical yield compared to hydrogen peroxide) and 4.9 g acetonezine (0.04 mole, which was a yield of 10%).

EXAMPLE 11

A mixture was prepared which comprised 145 g dicyclohexylamine (0.80 mole), 18 g of an aqueous solution containing 19.1 % by weight ammonia (0.20 mole), 46.4 g acetone (0.80 mole), 20.5 g acetonitrile (0.50 mole), and 64 g methanol, in which 1.2 g of the disodium salt of ethylene diaminetetracetic acid and 0.2 g of ammonium acetate were dissolved. The solution was brought to 450° C, and within the space of half an hour 19.45 g aqueous hydrogen peroxide containing 70% by weight $H_2O_2$ (0.40 mole) were introduced while a light current of gaseous ammonia was bubbled through the solution. The reaction was allowed to continue for four hours at the same temperature, and the mixture was then cooled to ambient temperature. A crystalline precipitate of the complex of the formula 2 (cyclohexylamine) $H_2O_2$ was then formed at the expense of the unconverted reactants, and this precipitate was filtered before distilling the solution under reduced pressure. A fraction of 13 g acetone N, N-dicycylohexylhydrazone (0.055 mole, which was 14% of the theoretical yield), which was identified by its infrared and mass spectra, was obtained.

EXAMPLE 12

A solution was prepared which comprised 206 g diisobutylamine (1.60 mole), 36 g an aqueous solution containing 19.1% by weight NH₃ (0.40 mole), 92.6 g acetone (1.60 mole), 41 g acetonitrile (1.00 mole), and 96 g metanol, in which 2.4 g of the disodium salt of ethylenediaminetetracetic acid and 0.4 g ammonium acetate were dissolved. The solution was brought to 50° C, and within the space of half an hour 38.9 g oxygenated water containing 70% by weight $H_2O_2$ (0.80 mole) were introduced. The reaction was allowed to continue for seven hours at the same temperature; and the solution was then distilled at 90° C and 20 mm Hg to obtain 26 g acetone N, N-diisobutylhydrazone (0.14 mole, which was 17.5% of the theoretical yield).

EXAMPLE 13

The procedure of Example 12 was repeated, except the diisobutylamine was replaced by 162 g diisopropylamine (1.60 mole). The resulting solution was distilled at 53–55° C and 10 mm Hg to obtain 20 g acetone N,N-diisopropylhydrazone (0.13 mole, which was 16% of the theoretical yield).

EXAMPLE 14

12.2 g of a 28% by weight aqueous solution of ammonia (0.20 mole) and 17.4 g acetone (0.30 mole) were added to a solution of 18.3 g p-nitroperbenzoic acid (0.10 mole), whose temperature was kept at 0° C. 22.5 g of a 40% by weight aqueous solution of dimethylamine (0.20 mole) were then introduced, and the solution was allowed to return to ambient temperature. After two hours, the solution was determined to contain 2.8 g acetone N,N-dimethylhydrazone (0.028 mole, which was 28% of the theoretical yield) and 0.34 g acetoneazine (0.003 mole, which was 3% yield).

EXAMPLE 15

A mixture was prepared which comprised 46.4 g acetone (0.8 mole), 74.5 g aniline (0.8 mole), 51.5 g benzonitrile (0.5 mole), 18 g of a 22% by weight aqueous solution of ammonia, 1.2 g of the disodium salt of ethylenediamine tetracetic acid, and 0.2 g ammonia acetate, and the whole mixture was homogenized with 48 g methanol (1.5 mole). The temperature of this solution was brought to 50° C, whereupon 19.4 g of a 70% by weight solution of hydrogen peroxide (0.4 mole) were added dropwise. After the solution reacted for 3 hours, during which gaseous NH₃ was continuously bubbled through, the reaction solution was determined to contain 26.8 g acetone phenylhydrazone (0.18 mole, which was a yield of 45% compared to the hydrogen peroxide used).

EXAMPLE 16

The procedure of Example 15 was repeated, except that the benzonitrile was replaced by propionitrile. After the solution reacted eight hours, it was determined to contain 29.8 g acetone phenylhydrazone (0.2 mole, which was a yield of 50% compared to the hydrogen peroxide used).

EXAMPLE 17

A mixture was prepared which comprised 149 g aniline (1.6 mole), 157 g cyclohexanone (1.6 mole), 41 g acetonitrile (1 mole), 36 g of a 19.1% by weight aqueous solution of ammonia (0.4 mole), 2.4 of the disodium salt of ethylenediaminetetracetic acid, 0.4 g ammonium acetate, and 160 g methanol (5 moles). The temperature was raised to 50° C, whereupon within a period of half an hour, 38.9 of a 70% by weight hydrogen peroxide solution were added dropwise. After the solution reacted for 6 hours, during which time gaseous ammonia was continuously bubbled through, it was determined to contain 11.6 g cyclohexnaone phenylhydrazone (0.06 mole, which was a yield of 7.7% compared to the hydrogen peroxide used).

EXAMPLE 18

A solution was prepared which comprised 23.2 g acetone, 10.2 g acetonitrile, 25.6 g p-chloroanline (0.2 mole), 9 g of a 19.1% by weight aqueous solution of ammonia, 0.6 g of the disodium salt of ethylenediaminetetracetic acid, 0.1 g ammonium acetate, and 96 g methanol (3 moles). This solution was brought to 50° C, and 9.7 g of a 70% by weight solution of hydrogen peroxide (0.2 mole) were added thereto within half an hour. After the solution reacted for 7 hours, during which time ammonia was continuously bubbled in, it was determined to contain 4.6 g acetone p-chlorophenylhydrazone (0.025 mole, which corresponded to a yield of 12.5% compared to the hydrogen peroxide used).

EXAMPLE 19

The procedure of Example 18 was repeated, except that p-chloroaniline was replaced by orthotoluidine. The reaction solution was determined to contain 6 g of acetone orthotolylhydrazone (0.037 mole, which corresponded to a yield of 18.5% compared to the hydrogen peroxide used).

EXAMPLE 20

The operation was carred out as in Example 3, except that the aniline was replaced by 25.5 g of p-chloroaniline (0.2 mole). The mixture was determined by gas chromatography to comprise 8.2 g acetone p-chlorophenylhydrazone (0.045 mole, which was 45% of the theoretical yield compared to the per-acid) and 0.96 g acetone azine (0.0086 mole, which was a yield of 8.6%).

EXAMPLE 21

The procedure of Example 3 was repeated, except that the aniline was replaced by 21.4 g orthotoluidine (0.2 mole). The solution was determined by gas chromatography to comprise 6.6 g aceto-orthomethylphenylhydrazne (0.041 mole, which was a theoretical yield of 41% compared to the per-acid) and 0.89 g acetoneazine (0.0079 mole, which was a yield of 7.9%).

EXAMPLE 22

The procedure of Example 3 was repeated, except that the aniline was replaced by 30.2 g methyl anthranilate (0.2 mole). The solution was determined by gas chromatography to contain 4.5 g methyl ortho(isopropylidenehydrazine)-benzoate (0.22 mole, which was a yield of 22% compared to the per-acid) and 2.8 g acetoneazine (0.025 mole, which was a yield of 25%).

EXAMPLE 23

The procedure of Example 3 was repeated, except that the aniline was replaced by 28.6 g β-naphthylamine (0.2 mole). Anaylsis by gas chromtography showed that 0.6 g acetone β-naphtylhydrazone (0.03 mole, which was a 3% yield compared to the per-acid) and 0.88 g acetonazine (0.008 mole, which was a yield of 8%) were formed.

EXAMPLE 24

The procedure of Example 3 was repeated, except that the acetone was replaced by 59 g cyclohexanone (0.6 mole). Analysis showed that 8.5 g cyclohexanone phenylhydrazone (0.45 mole, which was a yield of 45 % compared to the per-acid) and 0.77 g cyclohexanoneazine (0.004 mole, which was a yield of 4%) were formed.

EXAMPLE 25

The procedure of Example 3 was repeated, except that the acetone was replaced by 43.2 g (0.6 mole) methylethylketone. The solution was determined by gas chromatography to contain 40.5 g methylethylketone phenylhydrazone (0.025 mole, which was a yield of 25% compared to the per-acid) and 0.21 g methylethylketoneazine (0.0015 mole, which was a yield of 1.5%).

EXAMPLE 26

The procedure of Example 9 was repeated, except that the acetone was replaced by cyclogexanone. After the reaction, analysis of the mixture showed that 30 g cyclohexanone phenylhydrazone (0.16 mole, which was 32% of the theoretical yield) and 20 g cyclohexanoneazine (0.104 mole, which was a 20.8% yield) were formed.

EXAMPLE 27

The procedure of Example 9 was repeated, except that formamide was replaced by 37.5 g methyl formiate (0.625 mole). After the reaction, analysis of the mixture showed that 45G acetone phenylhydrazone (0.305 mole, which was 61% of the theoretical yield) and 5.3 g acetoneazine (0.048 mole, which was a 9.6% yield) were formed.

EXAMPLE 28

A solution was prepared which comprised 18.6 g aniline (0.2 mole), 11.6 g acetone (0.2 mole), 1.21 g of a 70% by weight solution of hydrogen peroxide (0.025 mole), 0.25 g of the disodium salt of ethylenediaminetetracetic acid, 18.1 g phthalimide (0.125 mole), and 0.85 g ammonia (0.05 mole) in 20 g methanol. This solution was brought to 50° C, and then within one hour 3.6 g of a 70% by weight of hydrogen peroxide were added while gaseous ammonia was bubbled through. After the solution reacted for 4 hours at the same temperature, it was determined by gas phase chromatography to contain 5.66 g acetone phenylhydrazone (0.038 mole, which was 38% of the theoretical yield) and 1.51 g acetoneazine (0.013 mole, which was a 13% yield).

EXAMPLE 29

A solution was prepared which comprised 18.6 g aniline (0.2 mole), 8.5 g ammonia (0.5 mole), 11.6 g acetone (0.2 mole), 0.25 g of the disodium salt of ethylenediaminetetracetic acid, and 4.9 g of a 70% by weight solution of hydrogen peroxide (0.1 mole) in 65 g methanol. This solution was brought to 0° C, and 18.5 g cyanuryl chloride (0.1 mole) were introduced into it within one hour while gaseous ammonia was bubbled through. After the solution reacted for 4 hours at the same temperature, it was determined by gas phase chromatography to contain 2.4 g acetone phenylhydrazone (0.016 mole, which was 16% of the theoretical yield) and 1.57 g acetoneazine (0.014 mole, which was a 14% yield).

We claim:

1. A method for preparing hydrazones which comprises reacting
   a. ammonia;
   b. an amine selected from methylamine, dimethylamine, ethylamine, diethylamine, n-propylamine, isopropylamine, n-butylamine, di-n-butylamine, t-butylamine, an amylamine, cyclohexylamine, dicyclohexylamine, n-dodecylamine, mono- and diethanoloamines, 2-methoxyethylamine, morpholine, pyrrolidine, piperidine, β-aminopropionitrile, β-aminopropionamide, aniline, a toluidine, mono- and dichloro-anilines and -toluidines, a bromoaniline, a fluoro-aniline, nitro- and diniutro-anilines and -toluidines, and anisidine, a trifluoromethylaniline, anthranilic acid, sulphanilic acid, diphenylamine, a naphthylamine and an aminopyridine;
   c. carbonyl compound selected from formaldehyde, acetaldehyde, propionaldehyde, butyraldehyde, isobutyraldehyde, n-pentanal, pivalaldehyde, oenanthal, 2-ethylhexanol, Δ-3-tetrahydrobenzaldehyde, hexahydrobenzaldehyde, 5-norbornene, 2-carboxyaldehyde, tetrahydropyran-2-carboxyaldehyde, benzaldehyde, a monochlorobenzaldehyde, p-nitrobenzaldehyde, β-chloropropionaldehyde, β-methoxypropionaldehyde, 4-cyano-2,2-dimethylbutyraldehyde acetone, 2-butanone, 2-pentanone, 3-pentanone, 3-pentanone, methylisopropylketone, methylisobutylketone, ethylamylketone, methylcyclohexylketone, acetophenone, benzophenone, cyclobutanone, cyclopentanone, cyclohexanone, a methylcyclohexanone, 2,4-dimethylcyclohexanone, 3,3,5-trimethylcyclohexanone, isophorone, cycloheptanone, cyclooctanone, cyclodecanone and cyclododecanone, and mixtures thereof; and
   d. a peroxide compound selected from (i) the percarboxylic acids of formic, acetic, propionic, butyric, isobutyric, valeric, isolvaleric, pivalic, hexanoic, heptanoic, octanoic, αα'-dimethyloctanoic, lauric, palmitic, stearic, hexahydrobenzoic, trifluoroacetic, β-chloropropionic, β-methoxypropionic, ε-hydroxycaproic, benzoic and its chlorine, bromine, fluorine, methoxyl, nitro, and trifluoro-methyl derivatives, a toluic, succinic, glutaric, adipic, crotonic, maleic, fumaric and phthalic acids; (ii) acetyl, monochloroacetyl, trifluoroacetyl, propionyl, β-chloropropionyl, β-methoxypropionyl, β-carboxypropionyl, n-butyryl, perfluoro-n-butyryl, isobutyryl, perfluorosobutyryl, crotonyl, valeryl, isovaleryl, pivaloyl, hexanoyl, heptanoyl, octanoyl, 2-ethylhexanoyl, noanoyl, decanoyl, lauroyl, myristoyl, palmitoyl, stearyl, cyclohexanecarbonyl, norbornane-2 carbonyl, benzoyl, o-toluyl-m-chlorobenzoyl, p-chlorobenzoyl, p-methoxybenzoyl, p-nitro-benzyol, m-trifluoromethyl-benzoyl, p-phenylbenzoyl, o-carboxyl-benzoyl, a naphthoyl, 2-furoyl and nicotinoyl peroxides and mixed acetyl and benzoyl peroxides, acetyl and butyryl peroxides, isobutyryl, and benzoyl peroxides, acetyl and lauroyl peroxides and stearyl and benzoyl peroxides; (iii) polymeric peroxides and mixed peroxides of oxalic, succinic, glutaric, adipic, pimelic, dodecanedioic, 1,2- or 3,4-cyclohexane dicarboxylic, o-phthalic, isophthalic, and terephthalic acids; (iv) isopropoxycarbonyl and benzoyl peroxide, methoxycarbonyl and lauroyl peroxide, 3,3,5-trimethylcyclohexyloxycarbonyl and lauroyl peroxide, and isopropyl peroxydicarbonate; mixed dianhydrides or diperoxy-carbonic and benzoyl, caproyl, lawcoyl, or 2-ethylhexanoyl; and (v) hydrogen peroxide in the presence of a catalyst selected from the chlorides, bromides, fluorides, nitrates, sulphates, phosphtates, chlorates, perchlorates, borates, carbonates, formiates, acetates, propionates, butyrates, isobutyrates, octanoates, benzoates, methanesulphonates, benzenesulphonates, and p-toluenesulphonates of lithium, sodium, potassium, magnesium, calcium, strontium, barium, ammonia, mono-, di-, and trialkylated amines in which the alkyl radicals contain from 1 to 12 carbon atoms, piperidine, morpholine, and pyrrolidine, or in the presence of a co-reactant selected from acetonitrile, propionitrile, butyronitrile, a tolunitrile, p-methoxybenzonitrile, chlorobenzonitrile, p-nitrobenzonitrile, mono-, di-, and trichloroacetonitrile, glycolonitrile, ε-hydroxycapronitrile, cyanacetic acid and its alkyl esters, β-cyanopropionic acid and its alkyl esters, β-cyanopyridine, nicotinic nitrile, isonicotinic nitrile, acrylonitrile, methacrylonitrile, crotononitrile, Δ-3-tetrahydrobenzonitrile, 3,4-epoxyhexahydrobenzonitrile, ββ'-dicyanoethylether, ββ'-dicyanoethyl sulphide, sulphoxide, or sulphone, cyanogen, malononitrile, succinontrile, glutaronitrile, adiponitrile, pimelonitride, suberonitrile, a phthalodinitrile, iminodiacetonitrile, nitrolotriacetonitrile, ethylenediamine, tetracetic acid nitrile, β-hydroxypropionitrile, βm-methoxyproionitrile, and the cyanoethyl derivatives of ethyleneglycol, glycerol, and sorbitol; formiates, acetates, monochloracetates, trichloroacetates, trifluoroacetates, propionates, butyrates, isobutyrates, valerates, hexanoates, octanoates, nonanoates, dodecanoates, benzoates, chlorobenzoates, p-methoxybenzoates, nitrobenzoates, oxalates, malonates, succinates, glutarates, adipates, pimelates, butane-1,2,4-tricarboxylates, o-phthalates, isophthalates, terephthalates, trimellitates, pyromellitates, β-hydroxypropionates, tartrates, and citrates of methanol, ethanol, n-propanol, isopropanol, n-butanol, isobutanol, 2-butanol, tertiary butanol, an amyl alcohol, n-hexanol, n-heptanol, n-octanol, 2-ethylhexanol, n-dodecanol, cyclohexanol, methylcyclohexanol, allyl alcohol, crotyl alcohol, Δ-3-tetrahydrobenzyl alcohol, benzyl alcohol, 2-methoxyethanol, 3-methoxypropanol, 2-ethoxyethanol, ethyleneglycol, propyleneglycol, glycerol, 1,1,1-trimethylolethane, pentaerythritol, sorbitol, phenol and its chlorine, bromine, nitro, and methoxyl derivatives, cresols, pyroatechlol; resorcinol and hydroquinone, β-propiolactone, Δ-butyrolactone, δ-valerolactone, ε-caprolactone, and their alkyl homoloques, formamides, monochloroacetamie, monobromoacetamide, dichloroacetamide, trichloroacetamide, trifluoroacetamide, β-chloropropionamide, αα-dichloropropionamide, α-bromopropionamide, perfluorobutyramide, glycolamide, lactamide, phenylacetamide and its derivatives halogenated in the core, diphenylacetamide, benzamide, o-toluamide, m-tolyamide, a chlorobenzamide, a bromobenzamide, a fluorobenzamide, perfluorobenzamide, a nitrobenzamide, salicylamide, p-hydroxybenzamide, the amic acids, diamides, and imides of oxalic, malonic, succinic, αα-dichlorosuccinic, malic, tartric, maleic, citric, itaconic, citraconic, o-phthalic, isophthalic, terephthalic, trimellitic, pyromellitic, and tetrachloro-o-phthalic acids; and the cyanides, cyanates, and thiocyanates of ammonium, alkali metals, and alkaline earth metals, magnesium and zinc, potassium ferrocyanide cyanogen chloride and bromide, cyanamide and its alkali metal and alkaline earth metal salts, the lower alkyl cyanates in which the alkyl group contains from 1 to about 6 carbon atoms, the phenyl cyanates, dicyandiamide, cyanuric halides, and melamine.

2. A method according to claim 1, in which the reaction takes place in a solvent medium.

* * * * *

UNITED STATES PATENT AND TRADEMARK OFFICE
CERTIFICATE OF CORRECTION

PATENT NO. : 3,943,132
DATED : March 9, 1976
INVENTOR(S) : JEAN-PIERRE SCHIRMANN ET AL.

It is certified that error appears in the above-identified patent and that said Letters Patent are hereby corrected as shown below:

Column 2, line 25, "$R_2^:$" should read -- $R_2$ --.

Column 3, line 18, after "unsubstituted" insert -- or substituted --;

line 22, "or", second occurrence, should read -- and --;

line 60, "a" should read -- the --.

Column 4, lines 29-30, delete "theylenic";

line 49, "$R_g(CN)_p$" should read -- $R_9(CN)_p$ --.

Column 5, line 13, after "carbon" insert -- atoms,--;

line 30, "coreactants" should read -- co-reactants --;

line 35, "coreactants" should read -- co-reactants --;

line 45, that portion of the equation reading "+(O)" should read -- +(O)⟶ --

UNITED STATES PATENT AND TRADEMARK OFFICE
CERTIFICATE OF CORRECTION

PATENT NO. : 3,943,132
DATED : March 9, 1976
INVENTOR(S) : JEAN-PIERRE SCHIRMANN ET AL.

It is certified that error appears in the above-identified patent and that said Letters Patent are hereby corrected as shown below:

Column 6, line 37, "and", second occurrence, should read

-- an --.

Column 7, line 4, should read:

butyraldehyde;
ketones: acetone, 2-butanone, ....

lines 32-33, "p-methoxybenoxyl" should read

-- p-methoxybenzoyl --;

lines 39-41, should read:

benzoyl peroxides;
polymeric peroxides (Vb) and mixed peroxides
of mono- and diacids (Vc) derived from HOOC-$R_8$-COOH
diacid: oxalic ....

lines 44-45, should read:

o-phthalic, isophthalic, terephthalic;
peroxides (Va) derived from carbonic acid, in which ....

line 50, should read:

ydicarbonate;
mixed peroxides (Va) such as the mixed ....

line 64, "pyrrolidine." should read

-- pyrrolidine; --.

UNITED STATES PATENT AND TRADEMARK OFFICE
CERTIFICATE OF CORRECTION

PATENT NO. : 3,943,132
DATED : March 9, 1976
INVENTOR(S) : JEAN-PIERRE SCHIRMANN ET AL.

It is certified that error appears in the above-identified patent and that said Letters Patent are hereby corrected as shown below:

Column 8, line 12, "βhydroxy-" should read -- β-hydroxy- --;

line 15, "tol." should read -- tol; --.

Column 9, line 7, "is" should read -- it --;

line 28, "amy" should read -- may --.

Column 10, line 12, "than" should read -- then --;

line 57, "has" should read -- had --;

line 58, "monopermaleat" should read

-- monopermaleate --.

Column 11, line 13, "0.197" should read -- 0.0197 --.

Column 12, line 10, "gaseouos" should read -- gaseous --;

line 11, "68%" should read -- 69% --;

line 50, "450°C" should read -- 50°C --;

line 68, after "36 g" insert -- of --.

Column 13, line 3, "metanol" should read -- methanol --;

line 40, "ethylenediamine tetracetic" should read -- ethylenediaminetetracetic --.

UNITED STATES PATENT AND TRADEMARK OFFICE
CERTIFICATE OF CORRECTION

PATENT NO. : 3,943,132
DATED : March 9, 1976
INVENTOR(S) : JEAN-PIERRE SCHIRMANN ET AL.

It is certified that error appears in the above-identified patent and that said Letters Patent are hereby corrected as shown below:

Column 14, line 4, "cyclohexnaone" should read -- cyclohexanone --;

line 10, "p-chloroanline" should read -- p-chloroaniline --;

lines 46-47, "aceto-orthomethylphenylhydrazne" should read -- aceto-orthomethylphenylhydrazone --;

line 65, "β-naphtylhydrazone" should read -- β-naphthylhydrazone --.

Column 15, line 15, "40.5g" should read -- 4.05g --;

line 47, after "weight" insert -- solution --.

Column 16, line 12, "ethanoloamines" should read -- ethanolamines --;

line 16, "diniutro-" should read -- dinitro- --;

line 20, after "c." insert -- a --;

line 30, delete "3-pentanone", second occurrence;

line 52, "perfluorosobutyryl" should read -- perfluoroisobutyryl --.

UNITED STATES PATENT AND TRADEMARK OFFICE
CERTIFICATE OF CORRECTION

PATENT NO. : 3,943,132
DATED : March 9, 1976
INVENTOR(S) : JEAN-PIERRE SCHIRMANN ET AL.

Page 5 of 5

It is certified that error appears in the above-identified patent and that said Letters Patent are hereby corrected as shown below:

Column 17, line 5, "lawcoyl" should read -- lauroyl --;

line 30, "pimelonitride" should read -- pimelonitrile --;

line 33, "βm-methoxyproionitrile" should read -- β-methoxypropionitrile --.

Column 18, line 13, "pyroatechlol" should read -- pyrocatechol --;

line 14, "Δ-butyrolactone" should read -- γ-butyrolactone --;

line 16, "homoloques" should read -- homologues -- and "monochloroacetamie" should read -- monochloroacetamide --.

Signed and Sealed this

Second Day of November 1976

[SEAL]

Attest:

RUTH C. MASON
*Attesting Officer*

C. MARSHALL DANN
*Commissioner of Patents and Trademarks*